(12) United States Patent
Algawi et al.

(10) Patent No.: US 12,285,360 B2
(45) Date of Patent: Apr. 29, 2025

(54) REDUCING IRRIGATION/ASPIRATION VALVE RESPONSE TIME IN A PHACOEMULSIFICATION SYSTEM

(71) Applicant: JOHNSON & JOHNSON SURGICAL VISION, INC., Irvine, CA (US)

(72) Inventors: Yehuda Algawi, Binyamina (IL); Assaf Govari, Haifa (IL); Eran Aharon, Haifa (IL); Ilya Sitnitsky, Nahariya (IL); Stanislav Katzir, Hadera (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 145 days.

(21) Appl. No.: 17/130,544

(22) Filed: Dec. 22, 2020

(65) Prior Publication Data
US 2022/0192877 A1    Jun. 23, 2022

(51) Int. Cl.
*A61F 9/007* (2006.01)
*A61B 17/00* (2006.01)
*A61M 39/22* (2006.01)

(52) U.S. Cl.
CPC ......... *A61F 9/00745* (2013.01); *A61M 39/22* (2013.01); *A61B 2017/00367* (2013.01);
(Continued)

(58) Field of Classification Search
CPC .. A61F 9/00745; A61F 9/00736; A61F 9/007; A61F 9/00781; A61F 9/00763;
(Continued)

(56) References Cited

U.S. PATENT DOCUMENTS 2,094,830 A * 10/1937 Clinton ................... F02B 75/22
                                                                123/63
3,393,566 A    7/1968 Malcolm et al.
(Continued)

FOREIGN PATENT DOCUMENTS

CN    108323001 A    7/2018
CN    110338970 A    10/2019
(Continued)

OTHER PUBLICATIONS

Cionni R.J., "Evaluating Two Key Safety Advances in the Centurion Vision System", ALCON, Cataract and Refractive Surgery Today, Aug. 2019, 4 pages.
(Continued)

*Primary Examiner* — Scott J Medway (57) ABSTRACT

A phacoemulsification apparatus includes a phacoemulsification probe, an electromechanical valve, and an electromechanical mechanism. The probe having a fluid channel for exchanging fluid with a patient's eye. The electromechanical valve is coupled with the fluid channel and is configured to regulate a fluid flow through the fluid channel. The valve including a cylinder, a piston inside the cylinder, wherein the piston divides the cylinder into a first cavity that is in fluid communication with the fluid channel, and a second cavity, and one or more fluid communication links, which are formed between the first and second cavities. The piston is configured to move inside the cylinder to regulate the flow of the fluid, and the one or more fluid communication links are configured to allow the fluid to flow between the first and second cavities during motion of the piston. The electromechanical mechanism is configured to move the piston.

19 Claims, 3 Drawing Sheets

(52) U.S. Cl.
CPC ... *A61B 2217/005* (2013.01); *A61B 2217/007* (2013.01); *A61M 2205/0272* (2013.01)

(58) Field of Classification Search
CPC .......... A61F 9/00754; A61F 2009/0087; A61F 2009/00887; A61F 9/00; A61F 2/16; A61M 1/0058; A61M 1/77; A61M 1/74; A61M 2210/0612; A61M 1/774; A61P 27/02; A61P 27/12; F04B 53/10; F04B 53/16; F04B 53/14; F04B 1/0408; F04B 23/06; F04B 49/03; F04B 1/0452; A61B 2017/00561; A61B 2217/007; A61B 2217/00

See application file for complete search history.

(56) References Cited

U.S. PATENT DOCUMENTS

| | | | |
|---|---|---|---|
| 3,575,301 | A | 4/1971 | Panissidi |
| 3,920,014 | A | 11/1975 | Banko |
| 3,994,421 | A * | 11/1976 | Hansen ............ A61M 15/0086 128/200.23 |
| 4,274,411 | A | 6/1981 | Dotson, Jr. |
| 4,291,706 | A * | 9/1981 | Voges .................. A61F 5/4405 600/580 |
| 4,653,719 | A | 3/1987 | Cabrera et al. |
| 4,702,733 | A | 10/1987 | Wright et al. |
| 4,818,186 | A | 4/1989 | Pastrone et al. |
| 4,832,685 | A | 5/1989 | Haines |
| 4,902,034 | A * | 2/1990 | Maguran .................. F16F 9/46 188/266.6 |
| 4,935,005 | A | 6/1990 | Haines |
| 4,954,960 | A | 9/1990 | Lo et al. |
| 5,032,111 | A | 7/1991 | Morris et al. |
| 5,047,009 | A | 9/1991 | Morris et al. |
| 5,106,367 | A | 4/1992 | Ureche et al. |
| 5,167,620 | A | 12/1992 | Ureche et al. |
| 5,190,042 | A | 3/1993 | Hock |
| 5,242,404 | A | 9/1993 | Conley et al. |
| 5,328,456 | A | 7/1994 | Horiguchi et al. |
| 5,354,268 | A | 10/1994 | Peterson et al. |
| 5,405,269 | A | 4/1995 | Stupecky |
| 5,476,448 | A | 12/1995 | Urich |
| 5,487,827 | A | 1/1996 | Peterson et al. |
| 5,569,188 | A | 10/1996 | Mackool |
| 5,591,127 | A | 1/1997 | Barwick, Jr. et al. |
| 5,616,120 | A | 4/1997 | Andrew et al. |
| 5,649,905 | A | 7/1997 | Zanger et al. |
| 5,695,473 | A | 12/1997 | Olsen |
| 5,697,898 | A | 12/1997 | Devine |
| 5,700,240 | A | 12/1997 | Barwick, Jr. et al. |
| 5,733,256 | A | 3/1998 | Costin |
| 5,766,146 | A | 6/1998 | Barwick, Jr. |
| 5,865,764 | A | 2/1999 | Moorhead |
| 5,885,243 | A | 3/1999 | Capetan et al. |
| 5,910,110 | A | 6/1999 | Bastable |
| 5,921,554 | A * | 7/1999 | Derian .................. F16J 15/162 277/516 |
| 5,935,106 | A | 8/1999 | Olsen |
| 6,050,496 | A | 4/2000 | Hefler |
| 6,159,175 | A | 12/2000 | Strukel et al. |
| 6,167,588 | B1 | 1/2001 | Dyson |
| 6,170,383 | B1 | 1/2001 | Mauritz |
| 6,179,808 | B1 | 1/2001 | Boukhny et al. |
| 6,190,354 | B1 | 2/2001 | Sell et al. |
| 6,383,203 | B1 * | 5/2002 | Makihara ............ A61F 9/00763 606/171 |
| 6,423,029 | B1 | 7/2002 | Elsberry |
| 6,491,661 | B1 | 12/2002 | Boukhny et al. |
| 6,533,747 | B1 | 3/2003 | Polaschegg et al. |
| 6,565,535 | B2 | 5/2003 | Zaias et al. |
| 6,579,255 | B2 | 6/2003 | Kadziauskas et al. |
| 6,599,271 | B1 | 7/2003 | Easley |
| 6,648,223 | B2 | 11/2003 | Boukhny et al. |
| 6,681,730 | B1 * | 1/2004 | Koneda .................... F01L 9/20 123/90.49 |
| 6,740,058 | B2 | 5/2004 | Lal et al. |
| 6,780,166 | B2 | 8/2004 | Kanda et al. |
| 6,986,753 | B2 | 1/2006 | Bui |
| 7,083,591 | B2 | 8/2006 | Cionni |
| 7,146,864 | B2 | 12/2006 | Sullivan et al. |
| 7,297,137 | B2 | 11/2007 | Gordon et al. |
| 7,785,336 | B2 | 8/2010 | Staggs |
| 8,246,580 | B2 | 8/2012 | Hopkins et al. |
| 8,380,126 | B1 | 2/2013 | Ma et al. |
| 8,430,841 | B2 | 4/2013 | Claus et al. |
| 8,479,585 | B2 | 7/2013 | Shaw-Klein |
| 8,523,812 | B2 | 9/2013 | Boukhny et al. |
| 8,617,106 | B2 | 12/2013 | Zacharias |
| 8,715,220 | B2 | 5/2014 | Gerg et al. |
| 8,721,594 | B2 | 5/2014 | Zacharias |
| 9,482,563 | B2 | 11/2016 | Calderin et al. |
| 9,549,851 | B2 | 1/2017 | Chon et al. |
| 9,610,193 | B2 | 4/2017 | Velasco et al. |
| 9,795,507 | B2 | 10/2017 | Hajishah et al. |
| 9,861,522 | B2 | 1/2018 | Sorensen et al. |
| 9,931,447 | B2 | 4/2018 | Layser et al. |
| 10,125,877 | B2 * | 11/2018 | Morgan ................ F16K 11/044 |
| 10,182,940 | B2 | 1/2019 | Chandrakant et al. |
| 10,278,861 | B2 | 5/2019 | Bourne |
| 10,500,319 | B2 | 12/2019 | Banko |
| 11,071,816 | B2 | 7/2021 | Mehta et al. |
| 11,383,020 | B2 | 7/2022 | Keh et al. |
| 2001/0023331 | A1 | 9/2001 | Kanda et al. |
| 2002/0019607 | A1 | 2/2002 | Bui |
| 2002/0174910 | A1 | 11/2002 | Willeke, Jr. et al. |
| 2003/0006729 | A1 | 1/2003 | Raymond |
| 2003/0050619 | A1 | 3/2003 | Mooijman et al. |
| 2003/0078487 | A1 | 4/2003 | Jeffries et al. |
| 2003/0105437 | A1 | 6/2003 | Neubert |
| 2004/0092885 | A1 | 5/2004 | Duchon et al. |
| 2004/0092921 | A1 | 5/2004 | Kadziauskas et al. |
| 2004/0101445 | A1 | 5/2004 | Shvets et al. |
| 2005/0080375 | A1 | 4/2005 | Kadziauskas et al. |
| 2005/0096593 | A1 | 5/2005 | Pope et al. |
| 2005/0118048 | A1 | 6/2005 | Traxinger |
| 2005/0209560 | A1 | 9/2005 | Boukhny et al. |
| 2005/0209621 | A1 | 9/2005 | Gordon et al. |
| 2005/0234441 | A1 | 10/2005 | Bisch et al. |
| 2005/0261628 | A1 | 11/2005 | Boukhny et al. |
| 2005/0261715 | A1 | 11/2005 | Boukhny et al. |
| 2005/0267504 | A1 | 12/2005 | Boukhny et al. |
| 2006/0058811 | A1 | 3/2006 | Kishimoto et al. |
| 2006/0224107 | A1 | 10/2006 | Claus et al. |
| 2006/0224143 | A1 | 10/2006 | Claus et al. |
| 2006/0224163 | A1 | 10/2006 | Sutton |
| 2006/0281986 | A1 | 12/2006 | Orilla et al. |
| 2007/0227265 | A1 | 10/2007 | Sugi et al. |
| 2007/0270744 | A1 * | 11/2007 | Dacquay ............... A61M 5/445 604/114 |
| 2008/0015406 | A1 | 1/2008 | Dlugos et al. |
| 2008/0033349 | A1 | 2/2008 | Suzuki |
| 2008/0053560 | A1 | 3/2008 | Hartman et al. |
| 2008/0112828 | A1 | 5/2008 | Muri et al. |
| 2008/0319374 | A1 | 12/2008 | Zacharias |
| 2008/0319451 | A1 | 12/2008 | Zacharias |
| 2009/0158855 | A1 | 6/2009 | Holden |
| 2009/0163863 | A1 | 6/2009 | Lutwyche |
| 2009/0302671 | A1 * | 12/2009 | Brooks .................... B60B 35/12 301/124.1 |
| 2010/0111735 | A1 * | 5/2010 | Tu ......................... F04B 53/127 222/190 |
| 2010/0145302 | A1 | 6/2010 | Cull et al. |
| 2010/0174238 | A1 * | 7/2010 | Sher ................ A61B 17/320758 606/159 |
| 2010/0280435 | A1 | 11/2010 | Raney et al. |
| 2010/0292631 | A1 * | 11/2010 | Holden ............... A61F 9/00745 604/22 |
| 2011/0027118 | A1 * | 2/2011 | Milovanovic ............ F01C 1/123 418/206.5 |
| 2011/0152728 | A1 | 6/2011 | Teodorescu |
| 2011/0284777 | A1 | 11/2011 | Pitchford et al. |
| 2011/0295191 | A1 | 12/2011 | Injev |

(56) References Cited

U.S. PATENT DOCUMENTS

| | | |
|---|---|---|
| 2011/0313343 A1 | 12/2011 | Milutinovic et al. |
| 2012/0004595 A1* | 1/2012 | Dubois ............ A61B 17/32002 |
| | | 606/49 |
| 2012/0041362 A1 | 2/2012 | Gerg et al. |
| 2013/0060210 A1* | 3/2013 | Ross ................... A61F 9/00736 |
| | | 604/319 |
| 2013/0062543 A1 | 3/2013 | Shiao et al. |
| 2013/0131578 A1 | 5/2013 | Stalmans et al. |
| 2013/0150782 A1 | 6/2013 | Sorensen et al. |
| 2013/0246079 A1 | 9/2013 | Hoffman et al. |
| 2014/0100518 A1 | 4/2014 | Baxter et al. |
| 2014/0107459 A1 | 4/2014 | Lind et al. |
| 2014/0114236 A1 | 4/2014 | Gordon et al. |
| 2014/0114237 A1 | 4/2014 | Gordon et al. |
| 2014/0163455 A1 | 6/2014 | Wilson et al. |
| 2014/0171869 A1 | 6/2014 | Zhang |
| 2014/0206940 A1 | 7/2014 | Hufford |
| 2014/0257172 A1 | 9/2014 | Yalamanchili |
| 2014/0282018 A1 | 9/2014 | Amble et al. |
| 2014/0323953 A1 | 10/2014 | Sorensen et al. |
| 2014/0364799 A1 | 12/2014 | Beauvais et al. |
| 2015/0057524 A1 | 2/2015 | Artsyukhovich et al. |
| 2015/0157501 A1 | 6/2015 | Bourne et al. |
| 2015/0359666 A1 | 12/2015 | Zacharias |
| 2016/0128869 A1 | 5/2016 | Zacharias |
| 2016/0175578 A1 | 6/2016 | Roholt |
| 2016/0220751 A1 | 8/2016 | Mallough et al. |
| 2016/0346123 A1 | 12/2016 | Koplin |
| 2016/0367735 A1 | 12/2016 | Eddo et al. |
| 2017/0022488 A1 | 1/2017 | Bermudez et al. |
| 2017/0224888 A1 | 8/2017 | Hickey et al. |
| 2017/0246419 A1 | 8/2017 | Callaghan et al. |
| 2017/0312431 A1 | 11/2017 | Johnson et al. |
| 2017/0367885 A1 | 12/2017 | Bourne |
| 2017/0367887 A1 | 12/2017 | Muri et al. |
| 2018/0028359 A1 | 2/2018 | Gordon et al. |
| 2018/0049920 A1 | 2/2018 | Charles |
| 2018/0078415 A1 | 3/2018 | Citterio |
| 2018/0279876 A1 | 10/2018 | Paschalis |
| 2018/0296738 A1 | 10/2018 | King et al. |
| 2018/0304012 A1* | 10/2018 | Jansen ................. B65B 7/2821 |
| 2019/0099526 A1 | 4/2019 | Hajishah et al. |
| 2019/0099529 A1 | 4/2019 | Mehta et al. |
| 2019/0099547 A1 | 4/2019 | Mehta et al. |
| 2019/0133822 A1 | 5/2019 | Banko |
| 2019/0143008 A1 | 5/2019 | Brundage et al. |
| 2019/0176557 A1 | 6/2019 | Marking et al. |
| 2019/0200885 A1 | 7/2019 | Jacobsen |
| 2019/0262175 A1 | 8/2019 | Kerkhoff et al. |
| 2019/0282401 A1 | 9/2019 | Sorensen et al. |
| 2019/0365567 A1 | 12/2019 | Balkenbush et al. |
| 2020/0030147 A1 | 1/2020 | Koplin |
| 2020/0107958 A1 | 4/2020 | Wong et al. |
| 2020/0337900 A1 | 10/2020 | Nazarifar et al. |
| 2021/0386927 A1 | 12/2021 | Mehta et al. |
| 2021/0386928 A1 | 12/2021 | Mehta et al. |
| 2022/0133537 A1 | 5/2022 | Govari et al. |
| 2022/0192876 A1 | 6/2022 | Algawi et al. |
| 2022/0193322 A1 | 6/2022 | Govari et al. |

FOREIGN PATENT DOCUMENTS

| | | |
|---|---|---|
| DE | 19753636 A1 | 9/1999 |
| EP | 1382291 A2 | 1/2004 |
| EP | 1471342 A2 | 10/2004 |
| EP | 1471342 B1 | 8/2009 |
| EP | 2379126 A2 | 10/2011 |
| EP | 2320842 B1 | 6/2012 |
| EP | 2164435 B1 | 8/2012 |
| JP | 62500640 T | 3/1987 |
| JP | 2001161740 A2 | 6/2001 |
| RU | 2720821 C1 | 5/2020 |
| WO | 8906522 A2 | 7/1989 |
| WO | 9945868 A1 | 9/1999 |
| WO | 0194893 A1 | 12/2001 |
| WO | 03047653 A1 | 6/2003 |
| WO | 04108189 A2 | 12/2004 |
| WO | 04110524 A2 | 12/2004 |
| WO | 2004108189 A2 | 12/2004 |
| WO | 05037156 A1 | 4/2005 |
| WO | 2007143797 A1 | 12/2007 |
| WO | 2008030872 A1 | 3/2008 |
| WO | 2008157674 A1 | 12/2008 |
| WO | 2009076717 A1 | 6/2009 |
| WO | 2011045033 A1 | 4/2011 |
| WO | 2011105909 A1 | 9/2011 |
| WO | 2016122790 A1 | 8/2016 |
| WO | 2016150754 A1 | 9/2016 |
| WO | 2016191665 A1 | 12/2016 |
| WO | 2019068151 A1 | 4/2019 |
| WO | 2019115584 A1 | 6/2019 |

OTHER PUBLICATIONS

Gopesh T., et al., "Rapid and Accurate Pressure Sensing Device for Direct Measurement of Intraocular Pressure", Translational Vision Science and Technology (TVST), Feb. 2020, vol. 9 (3), Article 28, pp. 1-9.

Miller K.M., et al., Millennialeye, Sep./Oct. 2019, Supplement to Cataract & Refractive Surgery Today, 16 pages.

Yao, J.L et al., "A Flexible and Highly Sensitive Piezoresistive Pressure Sensor Based on Micropatterned. Fihns Coated with Carbon Nanotubes, "Journal of Nanomaterials, 2016, pp. 1-6.

* cited by examiner

REDUCING IRRIGATION/ASPIRATION VALVE RESPONSE TIME IN A PHACOEMULSIFICATION SYSTEM

FIELD OF THE INVENTION

The present invention relates generally to phacoemulsification systems and probes, and particularly to valves of phacoemulsification systems.

BACKGROUND OF THE INVENTION

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

SUMMARY OF THE INVENTION

An embodiment of the present invention that is described hereinafter provides a phacoemulsification apparatus including a phacoemulsification probe, an electromechanical valve, and an electromechanical mechanism. The phacoemulsification probe includes a fluid channel for exchanging fluid with an eye of a patient. The electromechanical valve is coupled with the fluid channel and is configured to regulate a flow of the fluid through the fluid channel, the electromechanical valve including (a) a cylinder, (b) a piston inside the cylinder, wherein the piston divides the cylinder volume into a first cavity that is in fluid communication with the fluid channel, and a second, closed, cavity, and wherein the piston is configured to move inside the cylinder so as to regulate the flow of the fluid, and (c) one or more fluid communication links, which are formed between the first and second cavities, and configured to allow the fluid to flow between the first and second cavities during motion of the piston. The electromechanical mechanism is configured to move the piston.

In some embodiments, the fluid channel includes an irrigation channel for delivering irrigation fluid into the eye.

In some embodiments, the fluid channel includes an aspiration channel for evacuating emulsified lens material from the eye.

In an embodiment, the one or more fluid communication links include one or more slots on a surface of the cylinder. In another embodiment, the one or more fluid communication links include one or more slots on a surface of the piston.

In some embodiments, the one or more fluid communication links include one or more bores in the cylinder.

In some embodiments, the one or more fluid communication links include one or more bores in the piston.

In an embodiment, the electromechanical mechanism includes an electromagnet, and wherein the piston is magnetically-actuated.

In another embodiment, the valve is configured for one-time use.

There is additionally provided, in accordance with another embodiment of the present invention, a method for regulating fluid flow in a phacoemulsification system, including providing a phacoemulsification apparatus including a phacoemulsification probe including a fluid channel for exchanging fluid with an eye of a patient, an electromechanical valve that is coupled with the fluid channel, and an electromechanical mechanism, wherein the electromechanical valve includes (a) a cylinder, (b) a piston inside the cylinder, wherein the piston divides the cylinder volume into a first cavity that is in fluid communication with the fluid channel, and a second, closed, cavity, and wherein the piston is configured to move inside the cylinder so as to regulate the flow of the fluid, (c) one or more fluid communication links, which are formed between the first and second cavities, and configured to allow the fluid to flow between the first and second cavities during motion of the piston. The electromechanical valve is actuated with the electromechanical mechanism to cause the piston to move within the cylinder to regulate the fluid flow within the fluid channel.

In some embodiments, regulating the fluid flow within the fluid channel includes blocking the flow of fluid through the fluid channel.

The present invention will be more fully understood from the following detailed description of the embodiments thereof, taken together with the drawings in which:

DETAILED DESCRIPTION OF EMBODIMENTS

Overview

In phacoemulsification cataract surgery a surgeon uses a phacoemulsification probe, which has an ultrasonic handpiece with a needle. The tip of the needle vibrates at an ultrasonic frequency to sculpt and emulsify the cataract while a pump of the phacoemulsification system aspirates particles and fluid from the eye through the tip. Aspirated fluids are replaced by irrigation with a balanced salt solution (BSS) to maintain the anterior chamber of the eye.

In the phacoemulsification system, there may be valves that open and close the irrigation and/or the aspiration lines. Such valves typically need to be fast-acting, as well as leak-proof. Electromechanical valves, such as magnetically-actuated cylindrical valves, may be designed to be leak-proof by virtue of close tolerances between a central piston and a surrounding cylinder. However, such valves are slow-acting because the close tolerances effectively cause a vacuum to be formed in a cavity created as the piston moves, which resists piston motion.

Fast response is desired, however, to prevent hazard to the eye due to unstable intraocular pressure which may occur during phacoemulsification. One common scenario occurs, for example, when an emulsified particle blocks the inlet of the aspiration channel and increases the vacuum in the line. When the line later becomes unblocked (e.g., when the particle is subsequently sucked into the line), the high vacuum in the line causes an aspiration surge with potentially traumatic consequences to the eye. Using a valve to disconnect the aspiration line may be useful in preventing such a hazard if the valve action is fast enough.

Embodiments of the present invention that are described hereinafter provide valve designs for a phacoemulsification apparatus, which reduce valve response time. Valves designed accordingly may be incorporated to regulate a flow of fluid through a fluid channel (e.g., irrigation channel and/or aspiration channel), for example, in a standalone module that is detachably connected to a phacoemulsification handpiece, or they can be integrated in the handpiece itself. In the context of the present disclosure, the term "valve response time" or "switching time" is defined as the time duration taken by a valve piston to close an opened channel, or open a closed channel, such as an aspiration or irrigation channel.

In this description "regulate" is defined as adjusting the flow and/or blocking the flow.

In an embodiment, the disclosed valve is disposable (i.e., the valve is designed for one-time-use, possibly by being configured for use multiple times but only in a single clinical procedure, with the valve being disposed of afterwards). This valve can be used anywhere a valve can be used, and, more than one valve can be used in a system.

In the embodiments, a valve is provided that comprises a cylinder and a piston inside a cylinder, wherein the piston divides the cylinder volume into a first cavity that is in fluid communication with both an input port and an output port of a channel, and a second, closed, cavity. The piston is configured to move (e.g., bi-directionally) inside the cylinder, between a position that allows fluid to flow between the input and output ports and a position that blocks fluid from flowing between the input and output ports. One or more fluid communication links between the first and second cavities allow fluid to flow between the first and second cavities during piston motion.

In one embodiment, the one or more fluid communication links are slots in the cylinder surface surrounding the piston. Typically, the slots are parallel to a longitudinal axis of the cylinder (e.g., axis of symmetry). As the piston moves inside the cylinder in order to close the channel, liquid flows through the slots. The flow of liquid prevents the creation of a vacuum in the growing closed cavity volume that is formed in the cylinder on the other side of the piston that would otherwise cause drag, thereby allowing faster piston motion (i.e., reduced response time). The liquid flow also lubricates the piston motion.

As the piston moves to open the channel, pressured liquid flows from the closed cavity, thereby enabling the piston to return to its original position.

In another embodiment, the one or more fluid communication links are slots over the surface of the piston, instead of, or in addition to, the above-described slots in the cylinder. All slots serve the same purpose.

In a further embodiment, the one or more fluid communication links are small diameter bores in the piston. As the piston moves inside the cylinder to close the channel, liquid flows through the bores. The flow of liquid prevents any vacuum being formed in the cylinder on the other side of the piston.

In yet another embodiment, the one or more fluid communication links are bores in the bulk of the cylinder, instead of, or in addition to, bores made in the piston. The bores in the cylinder serve the same purpose: fluid communication between the two cavities of the cylinder. The bores may end with openings at the very ends of the cylinder (e.g., at its bases), to allow fluid coupling as long as the piston travels.

In an embodiment, the valve is comprised in a standalone disposable detachable add-on module for aspiration and irrigation control to reduce risks from irregular performance of aspiration and/or irrigation.

Typically, the piston is driven by an electromechanical mechanism. In one embodiment the piston is magnetically actuated.

By providing fast-acting valve designs, the disclosed embodiments of the invention may improve the safety and efficacy of phacoemulsification procedures, using, for example, existing probes and phacoemulsification systems.

System Description

Figure 1:
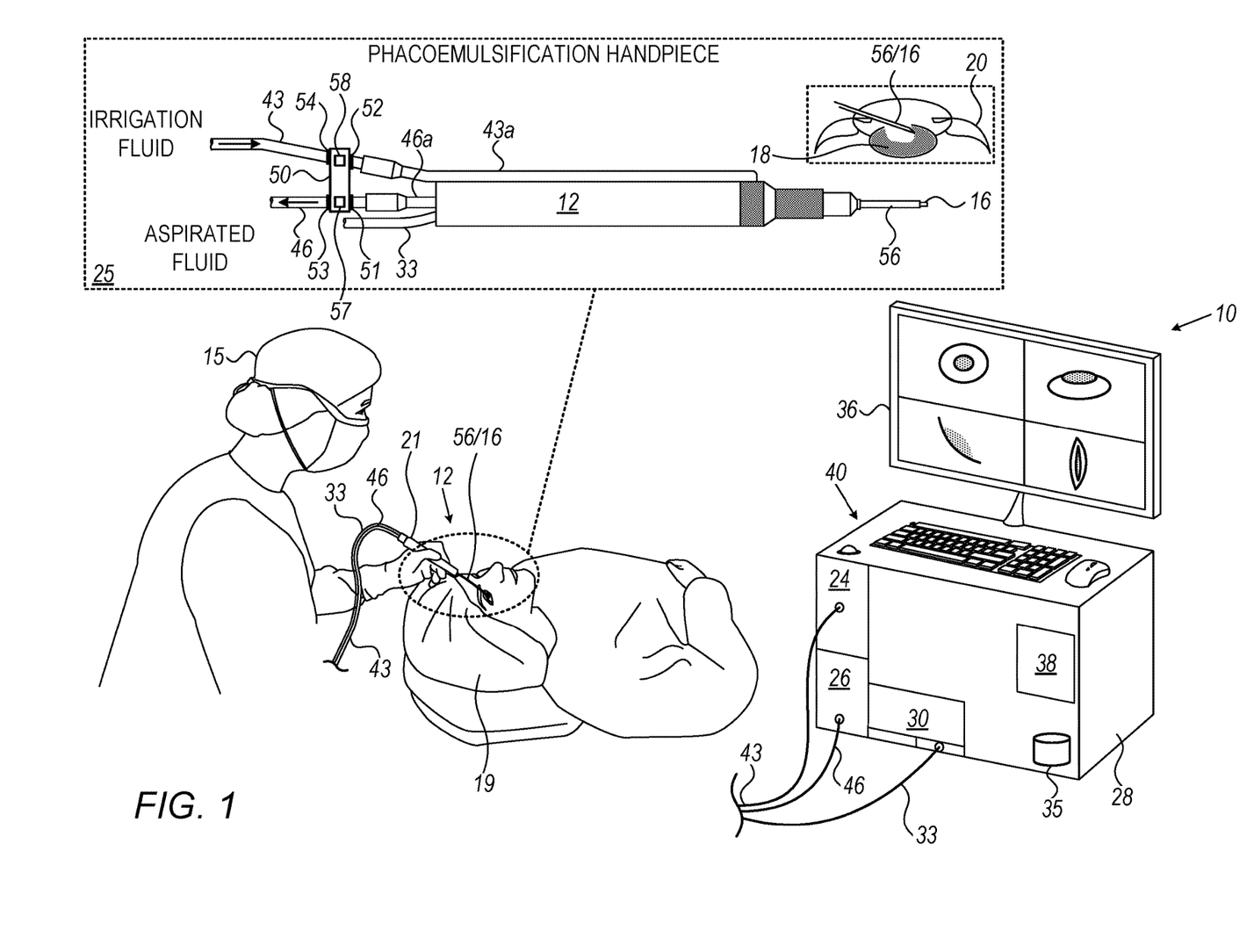
FIG. 1 is a schematic, pictorial view, along with an orthographic side view, of a phacoemulsification apparatus comprising valves for aspiration and irrigation control, in accordance with an embodiment of the present invention.

FIG. 1 is a schematic, pictorial view, along with an orthographic side view, of a phacoemulsification apparatus comprising valves 57 and/or 58 for aspiration and irrigation control, in accordance with an embodiment of the present invention. Valve 57 is configured to open/close an aspiration channel 46, whereas valve 58 is configured to open/close an irrigation channel 43.

In the example of apparatus 10 shown in FIG. 1, there is no link (e.g., bypass channel) between the irrigation and aspiration lines. As shown in FIG. 1, each of valves 57 and 58 regulates (e.g., blocks) the flow in a single line. In another embodiment, apparatus 10 may use only one linear valve, valve 57, for the aspiration line, which provides sufficient regulation to avoid hazard such as a vacuum surge. In such an embodiment valve 58 is omitted.

As seen in the pictorial view of phacoemulsification apparatus 10, and in inset 25, a phacoemulsification probe 12 (e.g., a handpiece) comprises a needle 16 and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, the irrigation sleeve may have one or more side ports at or near the distal end to allow irrigation fluid to flow toward the distal end of the handpiece through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, CA, USA.

In the shown embodiment, during the phacoemulsification procedure, a pumping subsystem 24 comprised in a console 28 pumps irrigation fluid from an irrigation reservoir to the irrigation sleeve 56 to irrigate the eye. The fluid is pumped via an irrigation tubing line 43 running from the console 28 to an irrigation channel 43a of probe 12. Eye fluid and waste matter (e.g., emulsified parts of the cataract) are aspirated via hollow needle 16 to the collection receptacle by a pumping subsystem 26, also comprised in console 28, using an aspiration tubing line 46 running from aspiration channel 46a of probe 12 to console 28. In another embodiment, the pumping subsystem 24 may be coupled or replaced with a gravity-fed irrigation source such as a BSS bottle/bag.

Apparatus 10 includes standalone disposable detachable add-on module 50, coupled via fluid connectors 51-54, to control aspiration and/or irrigation flow rates to reduce risks to eye 20 from irregular performance of aspiration and/or irrigation in probe 12, such as from a vacuum surge. To this end, the disclosed module 50 establishes, using one or more valves (e.g. a set of valves) inside module 50 comprising electromechanical valves 57 and 58, or using only a single valve 57 or valve 58, variable fluid communication between aspiration channel 46a and irrigation channel 43a to control the flow of fluid between the two channels/tubing lines, so as to maintain pressures in the two channels/tubing lines within prespecified limits. Moreover, module 50 can discontinue aspiration in parallel, e.g., using valve 57, in order to provide a fast response (e.g., closing aspiration channel 46a within several milliseconds) to a detected vacuum surge. Module 50 has its own processor, and can be used with existing phacoemulsification systems, as a disposable element, that improves control over intraocular pressure (IOP) during the surgical cataract removal procedure.

In another embodiment, an integrated disposable unit is provided which is built as a detachable assembly on the back handle, making the integrated disposable unit part of the handle. In this embodiment the handle is configured to connect with the integrated disposable part, rather than being connected via the tubes, as module 50 is.

In yet another embodiment, the integrated disposable unit does not necessarily include a processor, and the processor used for fluid regulation is located in console 28, with electrical wires connecting the integrated disposable unit and the processor.

Phacoemulsification probe 12 includes other elements (not shown), such as a piezoelectric crystal coupled with a horn to drive vibration of needle 16. The piezoelectric crystal is configured to vibrate needle 16 in a resonant vibration mode. The vibration of needle 16 is used to break a cataract into small pieces during a phacoemulsification procedure. Console 28 comprises a piezoelectric drive module 30, coupled with the piezoelectric crystal, using electrical wiring running in a cable 33. Drive module 30 is controlled by a processor 38 and conveys processor-controlled driving signals via cable 33 to, for example, maintain needle 16 at maximal vibration amplitude. The drive module may be realized in hardware or software, for example, in a proportional-integral-derivative (PID) control architecture.

Processor 38 may receive user-based commands via a user interface 40, which may include setting a vibration mode and/or frequency of the piezoelectric crystal, and setting or adjusting an irrigation and/or aspiration rate of the pumping subsystems 24/26. In an embodiment, user interface 40 and display 36 may be combined as a single touch screen graphical user interface. In an embodiment, the physician uses a foot pedal (not shown) as a means of control. Additionally, or alternatively, processor 38 may receive the user-based commands from controls located in a handle 21 of probe 12.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

In various embodiments, different electronic elements of module 50, such as valve 57 and 58 controllers, may be implemented using suitable hardware, such as one or more discrete components, one or more Application-Specific Integrated Circuits (ASICs) and/or one or more Field-Programmable Gate Arrays (FPGAs). In some embodiments, the different electronic elements also include driving electronics (e.g., high current electronic drivers) required to operate the valves. In other embodiments, the drivers are provided as part of electromechanical valves 57 and 58.

The apparatus shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

Reducing Valve Response Time

FIGS. 2A-2D comprise an isometric view accompanied with cross-sectional views of portion 200 of valve 57 of apparatus 10 of FIG. 1, in accordance with an embodiment of the present invention. Electromechanical valve 57 is included in module 50 of apparatus 10, as described above.

In an embodiment, (processor-controlled) valve 57 is configured to close an aspiration channel to, for example, immediately suppress a vacuum surge until regulated flows are restored by another mechanism of the system, e.g. the action of another valve inside module 50.

Figure 2A:
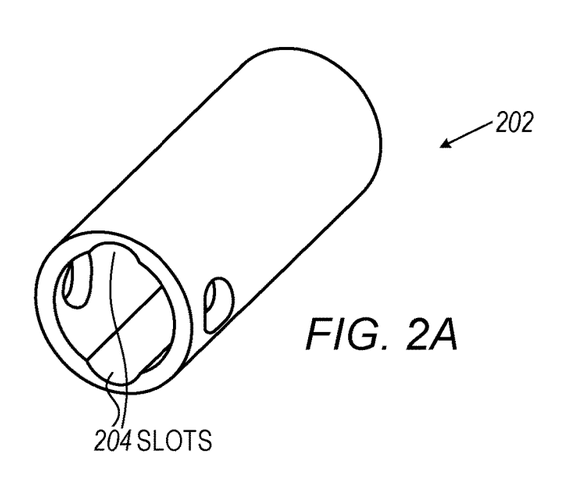
FIGS. 2A-2D comprises an isometric view, along with cross-sectional views of a portion of a valve of the apparatus of FIG. 1, in accordance with an embodiment of the present invention; and, FIGS. 3A-3D comprise an isometric view accompanied with cross-sectional views of a portion of a valve of the apparatus of FIG. 1, in accordance with another embodiment of the present invention.

FIG. 2A shows a cylinder 202 of a valve of the present invention, e.g. valve 57, to which slots 204 are introduced, that are parallel to a longitudinal axis of the cylinder (e.g., axis of symmetry).

Figure 2B:
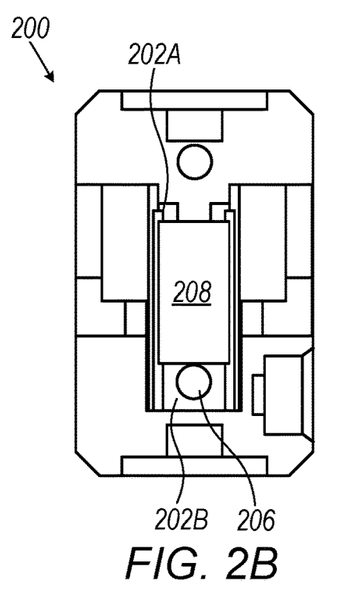
Figure 2C:
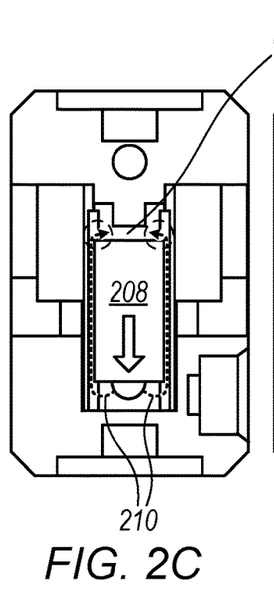
Figure 2D:
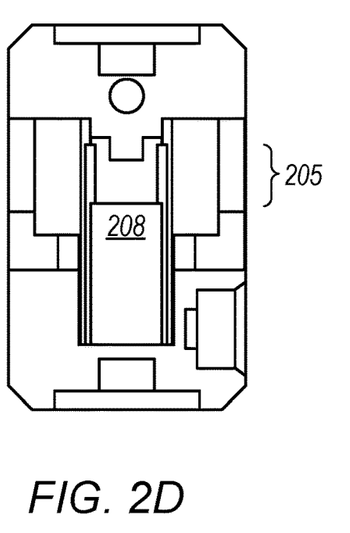

FIGS. 2B-2D show a piston 208 as it travels an interval 205 inside cylinder 202 to block a channel 206. As seen, as piston 208 travels, liquid flows (210) through the slots of cylinder 202 from one cavity (202B) to the other cavity (202A). The flow of liquid prevents any vacuum being formed in cavity 202A of the cylinder which may cause drag on piston 208 and slow piston motion. The liquid flow also lubricates the piston motion. This results in a reduced switching time, which is defined as the time a piston 208 takes to travel interval 205 to close channel 206.

The opposite piston motion, i.e., moving to open channel 206, is possible since fluid can flow through the slots in the opposite direction.

In another embodiment, the slots are made over the surface of piston 208, instead of, or in addition to, slots made in the cylinder. This, too, lets fluid flow as described above in FIGS. 2B-2D.

FIGS. 3A-3D comprise an isometric view accompanied with cross-sectional views of portion 300 of a valve that may be used in the apparatus of FIG. 1, in accordance with another embodiment of the present invention.

In the embodiment shown in FIGS. 3A-3D, one or more small diameter bores 306 are introduced in a piston 304 to establish fluid communication between cavities 302A and 302B of cylinder 302. Bore 306 can be used as an alternative to slots 204 of the embodiment shown in FIG. 2 or in addition to slots 204.

Figure 3A:
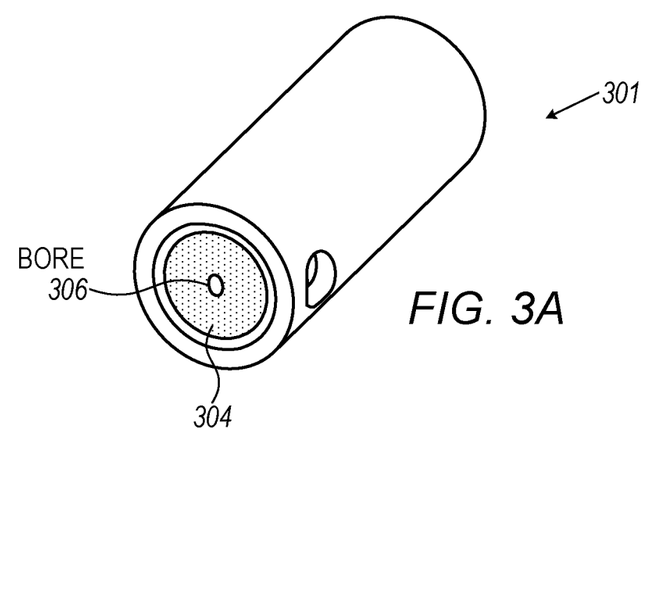

FIG. 3A shows a cylinder 301 of a valve of the present invention, e.g. valve 57, with a piston 304 inside, to which a bore 306 is introduced, that are parallel to a longitudinal axis of the piston (e.g., axis of symmetry).

Figure 3B:
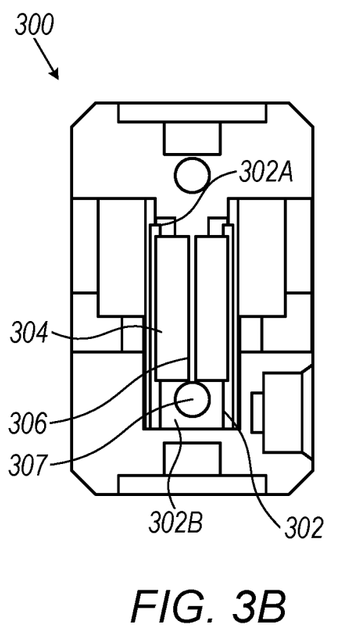
Figure 3C:
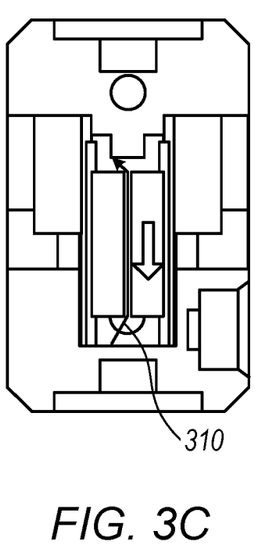
Figure 3D:
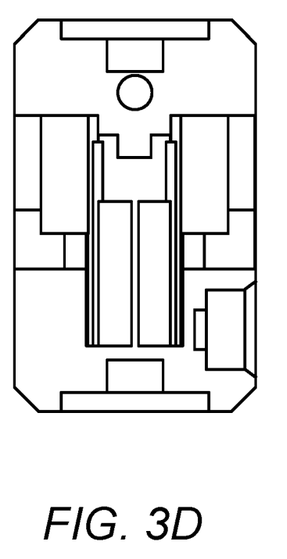

In FIGS. 3B-3D, as piston 304 moves inside cylinder 302 to close channel 307 (e.g., aspiration or irrigation channel), fluid flows (310) via bore 306 that can be one of one or more bores. As seen, as piston 304 travels, liquid flows (310) through the bores 306 from one cavity (302B) to the other cavity (302A), in a functionally similar manner to its flow in the embodiment of FIG. 2. The flow of liquid prevents any vacuum being formed in the cavity on the end of the piston, i.e., opposite to travel direction of piston 304. As a result, the time it takes for piston 304 to travel the required interval in either directions is reduced.

In another embodiment, the bores are made in cylinder 302 instead of, or in addition to, the bores in the piston. This also allows fluid flow, as described above, between the cavities as the piston moves.

The example solutions shown in FIGS. 2 and 3 are chosen purely for the sake of conceptual clarity. For example, other embodiments are possible, such as those that use a larger number of smaller diameter slots/bores, or slots/bores of different cross-sectional shapes (e.g., half round/v-grove slots, circular/rectangular bores). In addition, in an embodiment, a combination of one or more slots and one or more bores may be used to allow fluid flow from one cavity to another cavity. It is envisioned that any shape, size, or number of slots and/or bores may be used in the present invention.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification apparatus, comprising:
a phacoemulsification probe comprising a fluid channel for exchanging fluid with an eye of a patient; and
an electromechanical valve, which is coupled with the fluid channel and is configured to regulate a flow of the fluid through the fluid channel, the electromechanical valve comprising:
a cylinder;
a piston disposed inside the cylinder, wherein the piston divides a volume of the cylinder into a first cylinder cavity that is in fluid communication with both an input port and an output port of the fluid channel, and a second, closed, cylinder cavity, and wherein the piston is configured to be magnetically-actuated to move inside the cylinder so as to regulate the flow of the fluid through the fluid channel; and
one or more fluid communication links formed in at least one of a wall of the cylinder or formed in the piston between the first cylinder cavity and the second, closed cylinder cavity, and configured to allow an amount of the fluid to flow in the cylinder between the first cylinder cavity and the second, closed cylinder cavity, in a direction opposite of piston movement in the cylinder to reduce vacuum during motion of the piston; and
an electromechanical mechanism that is configured to move the piston.

2. The phacoemulsification apparatus according to claim 1, wherein the fluid channel comprises an irrigation channel for delivering irrigation fluid into the eye.

3. The phacoemulsification apparatus according to claim 1, wherein the fluid channel comprises an aspiration channel for evacuating emulsified lens material from the eye.

4. The phacoemulsification apparatus according to claim 1, wherein the one or more fluid communication links comprise one or more slots on a surface of the cylinder.

5. The phacoemulsification apparatus according to claim 1, wherein the one or more fluid communication links comprise one or more slots on a surface of the piston.

6. The phacoemulsification apparatus according to claim 1, wherein the one or more fluid communication links comprise one or more bores in the cylinder.

7. The phacoemulsification apparatus according to claim 1, wherein the one or more fluid communication links comprise one or more bores in the piston.

8. The phacoemulsification apparatus according to claim 1, wherein the electromechanical mechanism comprises an electromagnet to magnetically-actuate the piston.

9. The phacoemulsification apparatus according to claim 1, wherein the valve is configured for one-time use.

10. A method for regulating fluid flow in a phacoemulsification system, comprising:
providing a phacoemulsification apparatus comprising a phacoemulsification probe comprising a fluid channel for exchanging fluid with an eye of a patient, an electromechanical valve that is coupled with the fluid channel, and an electromechanical mechanism configured to drive the electromechanical valve,
wherein the electromechanical valve comprises:
a cylinder;
a piston disposed inside the cylinder, wherein the piston divides a volume of the cylinder into a first cylinder cavity that is in fluid communication with both an input port and an output port of the fluid channel, and a second, closed, cylinder cavity, and wherein the piston is configured to be magnetically-actuated to move inside the cylinder so as to regulate the flow of the fluid through the fluid channel; and
one or more fluid communication links formed in at least one of a wall of the cylinder or formed in the piston, between the first cylinder cavity and the second, closed cylinder cavity, and configured to allow an amount of the fluid to flow between the first cylinder cavity and the second closed cylinder cavity to reduce vacuum during motion of the piston; and
actuating the electromechanical valve with the electromechanical mechanism to cause the piston to move within the cylinder to regulate the fluid flow within the fluid channel.

11. The method of claim 10, wherein the fluid channel comprises an irrigation channel for delivering irrigation fluid into the eye.

12. The method of claim 10, wherein the fluid channel comprises an aspiration channel for evacuating emulsified lens material from the eye.

13. The method of claim 10, wherein the one or more fluid communication links comprise one or more slots on a surface of the cylinder.

14. The method of claim 10, wherein the one or more fluid communication links comprise one or more slots on a surface of the piston.

15. The method of claim 10, wherein the one or more fluid communication links comprise one or more bores in the cylinder.

16. The method of claim 10, wherein the one or more fluid communication links comprise one or more bores in the piston.

17. The method of claim 10, wherein the electromechanical mechanism comprises an electromagnet to magnetically-actuate the piston.

18. The method of claim 10, wherein the valve is configured for one-time use.

19. The method of claim 10, wherein regulating the fluid flow within the fluid channel comprises blocking the flow of fluid through the fluid channel.

\* \* \* \* \*